United States Patent
Berneth et al.

(10) Patent No.: US 6,737,142 B2
(45) Date of Patent: May 18, 2004

(54) OPTICAL DATA STORE COMPRISING AN AXIALLY SUBSTITUTED COBALT PHTHALOCYANINE IN THE LIGHT-WRITEABLE INFORMATION LAYER

(75) Inventors: Horst Berneth, Leverkusen (DE); Friedrich-Karl Bruder, Krefeld (DE); Wilfried Haese, Odenthal (DE); Rainer Hagen, Leverkusen (DE); Karin Hassenrück, Düsseldorf (DE); Serguei Kostromine, Swisttal (DE); Peter Landenberger, Köln (DE); Rafael Oser, Krefeld (DE); Thomas Sommermann, Bergisch Gladbach (DE); Josef-Walter Stawitz, Odenthal (DE); Thomas Bieringer, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/102,137

(22) Filed: Mar. 20, 2002

(65) Prior Publication Data
US 2002/0172793 A1 Nov. 21, 2002

(30) Foreign Application Priority Data

Mar. 28, 2001 (DE) .......................... 101 15 227
Sep. 28, 2001 (DE) .......................... 101 48 106

(51) Int. Cl.$^7$ ................................. B32B 3/02
(52) U.S. Cl. ................. 428/64.1; 428/64.8; 430/270.19; 430/270.2
(58) Field of Search ................. 428/64.1, 64.4, 428/64.8, 913; 430/270.14, 270.19, 270.2, 495.1, 945

(56) References Cited

U.S. PATENT DOCUMENTS

| 2,756,119 | A | 7/1956 | Baumann et al. ............... 8/34 |
| 3,636,049 | A | 1/1972 | Vollmann et al. ........ 260/314.5 |
| 5,248,538 | A | 9/1993 | Kovacs et al. ................ 428/64 |
| 6,399,768 | B1 | 6/2002 | Wolleb et al. ............... 540/140 |
| 2002/0099204 | A1 | 7/2002 | Wolleb et al. ............... 540/140 |

FOREIGN PATENT DOCUMENTS

| DE | 32 45 750 | 6/1984 |
| DE | 3622590 | 1/1987 |
| DE | 19 925 712 | 3/2004 |
| EP | 0 519 395 | 12/1992 |
| GB | 1 344 838 | 1/1974 |

OTHER PUBLICATIONS

Patent Abstracts of Japan vol. 011, No. 096 (C–412), Mar. 12, 1987 & JP 61 246393 A (Canon Inc), Nov. 1, 1986 Seite 3, allgemeine Formel Seite 4; Beispiel 1 Seite 5; Beispiel.

(List continued on next page.)

*Primary Examiner*—Elizabeth Mulvaney
(74) *Attorney, Agent, or Firm*—Godfried R. Akorli; Diderico van Eyl (57) ABSTRACT

Optical data carrier comprising a preferably transparent substrate which may, if desired, have previously been coated with one or more reflection layers and to whose surface a light-writeable information layer, if desired one or more reflection layers and if desired a protective layer or a further substrate or a covering layer have been applied, which can be written on and read by means of infrared light, preferably laser light, particularly preferably light having a wavelength in the range 750–800 nm, in particular 770–790 nm, where the information layer comprises a light-absorbent compound and, if desired, a binder, characterized in that at least one cobalt(III) phthalocyanine in which the Co metal centre bears two axial substituents $R^1$ and $R^2$ which represent, independently of one another, CN, SCN, alkoxy or alkylthio is used as light-absorbent compound.

12 Claims, 3 Drawing Sheets

OTHER PUBLICATIONS

Yahya H K et al: "Synthesis of Some Cobalt Phthalocyanine-3,3', 3,3'-Tetrasulphonamides and Spectroscopic Studies of Their Application to Cellulosic Fibres" Journal of the Society of Dyers and Colourists, Society of Dyers and Colourists. Bradford, GB, Bd. 104, Nr. 11, Nov. 1, 1988, Seiten 432–434, XP00025874 ISSN: 0037–9859 * Section Experimental *.

Angew. Chem. (month unavailable) 1978, pp. 927–1018, Von Klaus Deuchert und Siegfried Hünig, "Mehrstufige organische Redoxsysteme–ein allgemeines Struktruprinzip".

Topics in Current Chemistry, 92, ( month unavailable) 1980, pp. 1–44, Siegfried Hünig and Horst Berneth, "Two Step Reversible Redox Systems of the Weitz Type".

Takan s et al: "Ladder–type Phthalocyanine Conductor, PXXCO(PC) (CN)2 (PXX=Peri–Xanthe–noxanthene, Co(PC) (CN)2=Dicyano(Phthalocyaninato) Cobalt (III))" Chemistry Letters, Chemical Society of Japan. Tokyo, Jp Nr. 12, 1998, Seiten 1249–1250, XP000867757 ISSN: 0366–7022 Seite 1249, Zeile 20—Zeile 22.

OPTICAL DATA STORE COMPRISING AN AXIALLY SUBSTITUTED COBALT PHTHALOCYANINE IN THE LIGHT-WRITEABLE INFORMATION LAYER

The present invention relates to the use of an axially substituted cobalt phthalocyanine as light-absorbent compound in the light-writeable information layer of write-once optical data carriers, to optical data carriers and to a process for their production.

The write-once compact disk (CD-R) has recently experienced enormous volume growth. The light-absorbent compound of the information layer represents an important component of the optical data carrier and has to satisfy a variety of demanding requirements. The preparation of such compounds is not infrequently correspondingly costly (cf. WO-A-00/09522).

It is therefore an object of the invention to provide a simple-to-synthesize phthalocyanine dye which meets the demanding requirements (e.g. light stability, good signal/noise ratio, high writing sensitivity, damage-free application to the substrate material, etc.) for use as light-absorbent compound in the information layer of a write-once optical data carrier (especially a CD-R).

It has surprisingly been found that axially substituted cobalt phthalocyanines are very useful for this purpose.

The present invention accordingly provides an optical data carrier comprising a preferably transparent substrate which may, if desired, have previously been coated with one or more reflection layers and to whose surface a light-writeable information layer, if desired one or more reflection layers and if desired a protective layer or a further substrate or a covering layer have been applied, which can be written on and read by means of infrared light, preferably laser light, particularly preferably light having a wavelength in the range 750–800 nm, in particular 770–790 nm, where the information layer comprises a light-absorbent compound and, if desired, a binder, characterized in that at least one cobalt(III) phthalocyanine in which the Co metal centre bears two axial substituents $R^1$ and $R^2$ which represent, independently of one another, CN, SCN, alkoxy or alkylthio is used as light-absorbent compound.

As light-absorbent compound, preference is given to using a cobalt phthalocyanine of the formula (I)

(I)

where
CoPc represents cobalt(III) phthalocyanine, where $R^1$ and $R^2$ are axial radicals of the cobalt and the radicals $R^3$ to $R^6$ correspond to substituents of the phthalocyanine, where
$R^1$ and $R^2$ represent, independently of one another, CN, SCN, alkoxy or alkylthio,
$R^3$, $R^4$, $R^5$ and $R^6$ represent, independently of one another, halogen, cyano, alkyl, aryl, alkylamino, dialkylamino, alkoxy, alkylthio, aryloxy, arylthio, $SO_3H$, $SO_2NR^7R^8$, $CO_2R^{12}$, $CONR^7R^8$, $NH-COR^{12}$ or a radical $-(B)_m-D$, B is a bridge member selected from the group consisting of a direct bond, $CH_2$, CO, CH(alkyl), C(alkyl)$_2$, NH, S, O or $-CH=CH-$, where $(B)_m$ is a chemically realistic sequence of bridge members B and m=1 to 10, preferably 1, 2, 3 or 4,
D represents the monovalent radical of a redox system of the formula or or represents a metallocenyl radical or metallocenyl carbonyl radical in which the metal centre can be titanium, manganese, iron, ruthenium or osmium,
$X^1$ and $X^2$ represent, independently of one another, NR'R", OR" or SR",
$Y^1$ represents NR', O or S, $Y^2$ represents NR',
n represents a number from 1 to 10 and
R' and R" represent, independently of one another, hydrogen, alkyl, cycloalkyl, aryl or hetaryl or form a direct bond or a bridge to one of the carbon atoms of the chain, w, x, y and z represent, independently of one another, numbers from 0 to 4 and $w+x+y+z \leq 12$,
$R^7$ and $R^8$ represent, independently of one another, alkylamino, hydroxyalkylamino, dialkylamino, bishydroxyalkylamino or arylamino or $R^7$ and $R^8$ together with the N atom to which they are bound form a heterocyclic 5-, 6- or 7-membered ring, with or without participation of further heteroatoms, in particular from the group consisting of O, N and S, where $NR^7R^8$ represents, in particular, pyrrolidino, piperidino or morpholino,
$R^{12}$ represents alkyl, aryl, hetaryl or hydrogen,
Kat$^+$ represents a cation, in particular an alkali metal cation, ammonium cation, trialkylammonium cation, trialkyloxonium cation, triphenylcarbonium cation, diphenyliodonium cation, N-alkyl-pyridinium cation or a metallocenium cation, where the metal centre can be titanium, manganese, iron, ruthenium or osmium.

The alkyl, alkoxy, aryl and heterocyclic radicals may, if desired, bear further radicals such as alkyl, halogen, hydroxy, hydroxyalkyl, amino, alkylamino, dialkylamino, nitro, cyano, $CO-NH_2$, alkoxy, alkoxycarbonyl, morpholino, piperidino, pyrrolidino, pyrrolidono, trialkylsilyl, trialkylsiloxy or phenyl. The alkyl and alkoxy radicals may be saturated, unsaturated, straight-chain or branched, the alkyl radicals may be partially halogenated or perhalogenated, the alkyl and alkoxy radicals may be ethoxylated or propoxylated or silylated. Adjacent alkyl and/or alkoxy radicals on aryl or heterocyclic radicals may together form a three- or four-membered bridge.

Preference is given to compounds of the formula (I) in which, for the radicals $R^1$ to $R^8$ and R, R', R" and $R^{12}$:
Alkyl substituents are preferably $C_1-C_{16}$-alkyl, in particular $C_1-C_6$-alkyl, which may be unsubstituted or substituted by halogen such as chlorine, bromine or fluorine, hydroxy, cyano and/or $C_1-C_6$-alkoxy;
Alkoxy substituents are preferably $C_1-C_{16}$-alkoxy, in particular $C_1-C_6$-alkoxy which may be unsubstituted or substituted by halogen such as chlorine, bromine or fluorine, hydroxy, cyano and/or $C_1$–$C_6$-alkyl;

Cycloalkyl substituents are preferably $C_4$–$C_8$-cycloalkyl, in particular $C_5$–$C_6$-cycloalkyl, which may be unsubstituted or substituted by halogen such as chlorine, bromine or fluorine, hydroxy, cyano and/or $C_1$–$C_6$-alkyl;

Alkenyl substituents are preferably $C_6$–$C_8$-alkenyl, which may be unsubstituted or substituted by halogen such as chlorine, bromine or fluorine, hydroxy, cyano and/or $C_1$–$C_6$-alkyl, where alkenyl is particularly preferably allyl;

Hetaryl substituents are preferably heterocyclic radicals having 5- to 7-membered rings which preferably contain heteroatoms from the group consisting of N, S and/or O and may be fused to aromatic rings or may bear further substituents, for example halogen, hydroxy, cyano and/or alkyl, with particular preference being given to: pyridyl, furyl, thienyl, oxazolyl, thiazolyl, imidazolyl, quinolyl, benzoxazolyl, benzothiazolyl and benzimidazolyl;

Aryl substituents are preferably $C_6$–$C_{10}$-aryl, in particular phenyl or naphthyl, which may be unsubstituted or substituted by halogen such as F or Cl, hydroxy, $C_1$–$C_6$-alkyl, $C_1$–$C_6$-alkoxy, $NO_2$ and/or CN.

Preference is given to cobalt phthalocyanines of the formula (I) in which $R^3$, $R^4$, $R^5$ and $R^6$ represent, independently of one another, chlorine, fluorine, bromine, iodine, cyano, methyl, ethyl, propyl, isopropyl, butyl, isobutyl, tert-butyl, pentyl, tert-amyl, hydroxyethyl, 3-dimethylaminopropyl, 3-diethylaminopropyl, phenyl, p-tert-butylphenyl, p-methoxyphenyl, isopropylphenyl, trifluoromethylphenyl, naphthyl, methylamino, ethylamino, propylamino, isopropylamino, butylamino, isobutylamino, tert-butylamino, pentylamino, tert-amylamino, benzylamino, methylphenylhexylamino, hydroxyethylamino, aminopropylamino, aminoethylamino, 3-dimethylaminopropylamino, 3-diethylaminopropylamino, diethylaminoethylamino, dibutylaminopropylamino, morpholinopropylamino, piperidinopropylamino, pyrrolidinopropylamino, pyrrolidonopropylamino, 3-(methylhydroxyethylamino)propylamino, methoxyethylamino, ethoxyethylamino, methoxypropyl-amino, ethoxypropylamino, methoxyethoxypropylamino, 3-(2-ethylhexyloxy)propylamino, isopropyloxypropylamino, dimethylamino, diethylamino, diethanolamino, dipropylamino, diisopropylamino, dibutylamino, diisobutylamino, di-tert-butylamino, dipentylamino, di-tert-amylamino, bis(2-ethylhexyl)amino, bis(aminopropyl)amino, bis(aminoethyl)amino, bis(3-dimethylaminopropyl)amino, bis(3-diethylaminopropyl)amino, bis(diethylaminoethyl)amino, bis(dibutylaminopropyl)amino, di(morpholino-propyl)amino, di(piperidinopropyl)amino, di(pyrrolidinopropyl)amino, di(pyrrolidonopropyl)amino, bis(3-(methyl-hydroxyethylamino)propyl)amino, dimethoxyethylamino, diethoxyethylamino, dimethoxypropylamino, diethoxypropylamino, di(methoxyethoxyethyl)amino, di(methoxyethoxypropyl)amino, bis(3-(2-ethylhexyloxy)propyl)amino, di(isopropyloxy-isopropyl)amino, methoxy, ethoxy, propyloxy, isopropyloxy, butyloxy, isobutyloxy, tert-butyloxy, pentyloxy, tert-amyloxy, methoxyethoxy, ethoxyethoxy, methoxypropyloxy, ethoxypropyloxy, methoxyethoxypropyloxy, 3-(2-ethylhexyloxy)propyloxy, methylthio, ethylthio, propylthio, isopropylthio, butylthio, isobutylthio, tert-butylthio, pentylthio, tert-amylthio, phenyl, methoxyphenyl, trifluoromethylphenyl, naphthyl, $CO_2R^{12}$, $CONR^7R^8$, $NH-COR^{12}$, $SO_3H$, $SO_2NR^7R^8$, or a radical of the formula where $(B)_m$ represents where the asterisk (*) indicates the point of linkage to the 5-membered ring, M represents Mn or Fe, w, x, y and z represent, independently of one another, numbers from 0 to 4 and $w+x+y+z \leq 12$, $Kat^+$ represents a lithium cation, sodium cation, potassium cation, tetrabutylammonium cation, tetrapropylammonium cation, tetraethylammonium cation, tetramethylammonium cation, triethyloxonium cation, triphenylcarbonium cation, diphenyliodonium cation, N-ethylpyridinium cation or ferrocenium cation, $NR^7R^8$ represents amino, methylamino, ethylamino, propylamino, isopropylamino, butylamino, isobutylamino, tert-butylamino, pentylamino, tert-amylamino, benzyl amino, methylphenylhexylamino, 2-ethyl-1-hexylamino, hydroxyethylamino, aminopropylamino, aminoethylamino, 3-dimethylaminopropylamino, 3-diethylaminopropylamino, morpholinopropylamino, piperidino-propylamino, pyrrolidinopropylamino, pyrrolidonopropylamino, 3-(methyl-hydroxyethylamino)propylamino, methoxyethylamino, ethoxyethylamino, methoxypropylamino, ethoxypropylamino, methoxyethoxypropylamino, 3-(2-ethylhexyloxy)propylamino, isopropyloxyisopropylamino, dimethylamino, diethylamino, dipropylamino, diisopropylamino, dibutylamino, diisobutylamino, di-tert-butylamino, dipentylamino, di-tert-amylamino, bis(2-ethylhexyl)amino, dihydroxyethylamino, bis(aminopropyl)amino, bis(aminoethyl)amino, bis(3-dimethylaminopropyl)amino, bis(3-diethylaminopropyl)amino, di(morpholinopropyl)amino, di(piperidinopropyl)amino, di(pyrrolidinopropyl)amino, di(pyrrolidonopropyl)amino, bis(3-(methyl-hydroxyethylamino)propyl)amino, dimethoxyethylamino, diethoxyethylamino, dimethoxypropylamino, diethoxypropylamino, di(methoxyethoxypropyl)amino, bis(3-(2- ethylhexyloxy)propyl)amino, di(isopropyloxyisopropyl)amino, anilino, p-toluidino, p-tert-butylanilino, p-anisidino, isopropylanilino or naphthylamino or $NR^7R^8$ represents pyrrolidino, piperidino, piperazino or morpholino, $R^{12}$ represents hydrogen, methyl, ethyl, propyl, isopropyl, butyl, isobutyl, tertbutyl, pentyl, tert-amyl, phenyl, p-tert-butylphenyl, p-methoxyphenyl, isopropylphenyl, p-trifluoromethylphenyl, cyanophenyl, naphthyl, 4-pyridinyl, 2-pyridinyl, 2-quinolinyl, 2-pyrrolyl or 2-indolyl, where the alkyl, alkoxy, aryl and heterocyclic radicals may, if desired, bear further radicals such as alkyl, halogen, hydroxy, hydroxyalkyl, amino, alkylamino, dialkylamino, nitro, cyano, $CO-NH_2$, alkoxy, alkoxycarbonyl, morpholino, piperidino, pyrrolidino, pyrrolidono, trialkylsilyl, trialkylsiloxy or phenyl, the alkyl and/or alkoxy radicals may be saturated, unsaturated, straight-chain or branched, the alkyl radicals may be partially halogenated or perhalogenated, the alkyl and/or alkoxy radicals may be ethoxylated or propoxylated or silylated, adjacent alkyl and/or alkoxy radicals on aryl or heterocyclic radicals may together form a three- or four-membered bridge.

For the purposes of the present application, redox systems are, in particular, the redox systems described in Angew. Chem. 1978, p. 927, and in Topics of Current Chemistry, Vol. 92, p. 1 (1980).

Preference is given to p-phenylenediamines, phenothiazines, dihydrophenazines, bipyridinium salts (viologens), quinodimethanes.

Particular preference is given to cobalt phthalocyanines of the formula (I) which correspond to the formula (Ic).

In addition, the invention provides cobalt(III) phthalocyanines whose Co metal centre bears two axial substituents $R^1$ and $R^2$ which represent, independently of one another, CN, SCN, alkoxy or alkylthio and whose phthalocyanine radical is substituted.

These are preferably cobalt phthalocyanines of the formula (I) in which the sum of w, x, y and z is greater than zero, preferably a number from 1 to 12.

Very particular preference is given to compounds according to the invention which have the formula Ic (Ic)

where

Halogen represents chlorine, bromine or fluorine,

Alkoxy represents $C_1$–$C_8$-alkoxy which may be substituted or unsubstituted and a represents a number from 0 to 4, b represents a number from 0 to 10, c represents a number from 0 to 8, where the sum of a, b and c is ≦12 and $R^1$, $R^2$, $R^7$, $R^8$, $Kat^+$ and CoPc are as defined above.

The invention also provides a process for preparing compounds of the formula (Ic) which is characterized in that a cobalt phthalocyanine which is substituted by sulphonamide groups of the formula $SO_2NR^7R^8$, where $R^7$ and $R^8$ are as defined above, and may be substituted by halogen and/or alkoxy radicals is oxidized and reacted with KatCN, KatSCN, Katalkoxy or Katalkylthio.

The preparation is preferably carried out starting from an unsubstituted or halogen- and/or alkoxy-substituted cobalt phthalocyanine by sulphochlorination using chlorosulphonic acid and thionyl chloride at 50–130° C. and reaction with the appropriate amine to form the amide in water at pH=8–12 and at from room temperature to 100° C. The subsequent introduction of the axial amine substituents is preferably carried out in a known manner under oxidative conditions, e.g. chlorine or air, preferably air, in the case of air in the presence of excess KatCN, KatSCN, Katalkoxy or Katalkylthio.

The light-writeable information layer particularly preferably comprises, as light-absorbent compounds, one of the above-described cobalt(III) phthalocyanine compounds, in particular one of the formula I, together with at least one further substituted or unsubstituted phthalocyanine, hereinafter referred to as component b), with or without a central atom. Possible central atoms for this component are, for example, atoms selected from the group consisting of Si, Zn, Al, Cu, Pd, Pt, Au and Ag, in particular Cu and Pd.

The invention therefore also provides mixtures comprising a) a cobalt(III) phthalocyanine whose Co metal centre bears two axial substituents $R^1$ and $R^2$ which represent, independently of one another, CN, SCN, alkoxy or alkylthio and b) a phthalocyanine different from a), in particular a Co-free phthalocyanine.

For the components a) and b), preference is given to the preferred embodiments mentioned above in each case.

Particularly preferred components b) are, for example, the sulphonamide-substituted copper phthalocyanines known from DE-A 19 925 712. Particular preference is given to those of the formula II (II)

where

CuPc is a copper phthalocyanine radical,

A represents a substituted or unsubstituted, straight-chain or branched $C_2$–$C_6$-alkylene such as ethylene, propylene, butylene, pentylene, hexylene, $R^9$ and $R^{10}$ represent, independently of one another, hydrogen or substituted or unsubstituted, straight-chain or branched $C_1$–$C_6$-alkyl such as methyl, ethyl, propyl, butyl, pentyl, hexyl, in particular substituted $C_1$–$C_6$-hydroxyalkyl or unsubstituted $C_1$–$C_6$-alkyl, or $R^1$ and $R^2$ together with the N atom to which they are bound form a heterocyclic 5- or 6-membered ring which may, if desired, contain a further heteroatom, e.g. S, N or O, x represents a number from 2.0 to 4.0, y represents a number from 0 to 1.5 and the sum of x and y is from 2.0 to 4.0, preferably from 2.5 to 4.0.

Particularly preferred components b) in the mixture are compounds of the formula (II) which correspond to the formula (IIa)

(IIa), where
CuPc is copper phthalocyanine.

Further preferred additional light-absorbent compounds are the sulphonamide- or amido-substituted phthalocyanines which are known from, for example, EP-A-519 395.

In the case of mixtures of various light-absorbent compounds, the proportion of compounds of the formula (1) in the mixture is preferably from 10 to 90% by weight.

Particular preference is given to a mixture of compounds of the formulae (I) and (II) in a weight ratio of from 10:90 to 90:10, preferably from 20:80 to 80:20, particularly preferably from 40:60 to 60:40.

The information layer can comprise not only the light-absorbent compound but also binders, wetting agents, stabilizers, diluents and sensitizers and also further constituents.

The substrates can have been produced from optically transparent plastics which, if necessary, have undergone a surface treatment. Preferred plastics are polycarbonates and polyacrylates, and also polycycloolefins or polyolefins.

The reflection layer can have been produced from any metal or metal alloy which is customarily utilized for writeable optical data carriers. Suitable metals or metal alloys can be vapour deposited and sputtered and comprise, for example, gold, silver, copper, aluminum and their alloys with one another or with other metals.

The possible protective layer over the reflection layer can comprise UV-curable acrylates.

A possible intermediate layer which protects the reflection layer, for example from oxidation, may likewise be present.

The invention likewise provides a process for producing the optical data carriers of the invention, which is characterized in that the light-writeable information layer is applied to a transparent substrate by coating with at least one cobalt phthalocyanine complex of the formula I, if desired in combination with other light-absorbent compounds, in particular those of the component b), suitable binders, additives and solvents, and this coated substrate is provided, if desired, with a reflection layer, if desired further intermediate layers and, if desired, a protective layer.

Coating of the substrate with the light-absorbent compound of the formula I, if desired in combination with further dyes, binders and/or solvents, is preferably carried out by spin coating or sputtering.

To carry out the coating procedure, the light-absorbent compound of the formula I, with or without additives, is preferably dissolved in a suitable solvent or solvent mixture so that the compound of the formula I is present in an amount of 100 parts by weight or less, for example from 10 to 20 parts by weight, per 100 parts by weight of solvent. The writeable information layer is then metallized (reflection layer) by sputtering or vapour deposition, preferably under reduced pressure, and may subsequently be provided with a protective coating (protective layer) or a further substrate or a covering layer. Multilayer assemblies which have a partially transparent reflection layer are also possible.

Solvents or solvent mixtures for coating with the light-absorbent compounds of the formula I or mixtures thereof with additives and/or binders and also other light-absorbent compounds are chosen, firstly, on the basis of their solvent capacity for the light-absorbent compound of the formula I and the other additives and, secondly, so that they have a minimum influence on the substrate. Suitable solvents which have little influence on the substrate are, for example, alcohols, ethers, hydrocarbons, halogenated hydrocarbons, alkoxyalcohols, ketones. Examples of such solvents are methanol, ethanol, propanol, 2,2,3,3-tetrafluoropropanol, butanol, diacetone alcohol, benzyl alcohol, tetrachloroethane, dichloromethane, diethyl ether, dipropyl ether, dibutyl ether, methyl tert-butyl ether, methoxyethanol, ethoxyethanol, 1-methyl-2-propanol, methyl ethyl ketone, 4-hydroxy-4-methyl-2-pentanone, hexane, cyclohexane, ethylcyclohexane, octane, benzene, toluene, xylene. Preferred solvents are hydrocarbons and alcohols, since they have the least influence on the substrate.

Suitable additives for the writeable information layer are stabilizers, wetting agents, binders, diluents and sensitizers.

The light-absorbent compound should preferably be able to be changed thermally. The thermal change preferably occurs at a temperature of <600° C. Such a change can be, for example, a decomposition or chemical change of the chromophoric centre of the light-absorbent compound.

Apart from the information layer, further layers such as metal layers, dielectric layers and protective layers may be present in the optical data carrier. Metal and dielectric layers serve, inter alia, to adjust the reflectivity and the heat absorption/retention. Metals can be, depending on the laser wavelength, gold, silver, aluminium, etc. Examples of dielectric layers are silicon dioxide and silicon nitride. Protective layers are, for example, photocurable surface coatings, (pressure-sensitive) adhesive layers and protective films.

Pressure-sensitive adhesive layers consist mainly of acrylic adhesives. Nitto Denko DA-8320 or DA-8310, disclosed in the patent JP-A 11-273147, can, for example, be used for this purpose.

The optical data carrier has, for example, the following layer structure (cf. FIG. 1): a transparent substrate (1), if desired a protective layer (2), an information layer (3), if desired a protective layer (4), if desired an adhesive layer (5), a covering layer (6).

Figure 1:
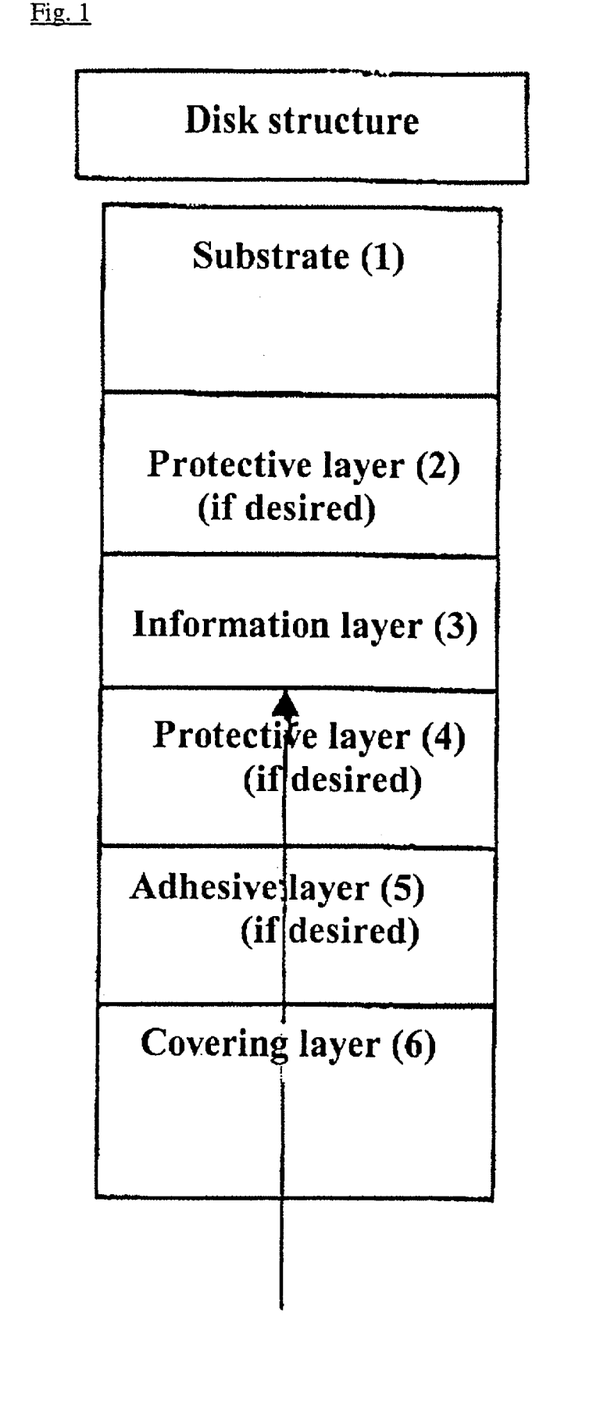

The structure of the optical data carrier preferably:

comprises a preferably transparent substrate (1) to whose surface at least one light-writeable information layer (3) which can be written on by means of light, preferably laser light, if desired a protective layer (4), if desired an adhesive layer (5) and a transparent covering layer (6) have been applied.

comprises a preferably transparent substrate (1) to whose surface a protective layer (2), at least one information layer (3) which can be written on by means of light, preferably laser light, if desired an adhesive layer (5) and a transparent covering layer (6) have been applied.

comprises a preferably transparent substrate (1) to whose surface a protective layer (2) if desired, at least one information layer (3) which can be written on by means of light, preferably laser light, if desired a protective layer (4), if desired an adhesive layer (5) and a transparent covering layer (6) have been applied.

comprises a preferably transparent substrate (1) to whose surface at least one information layer (3) which can be written on by means of light, preferably laser light, if desired an adhesive layer (5) and a transparent covering layer (6) have been applied.

Figure 2:
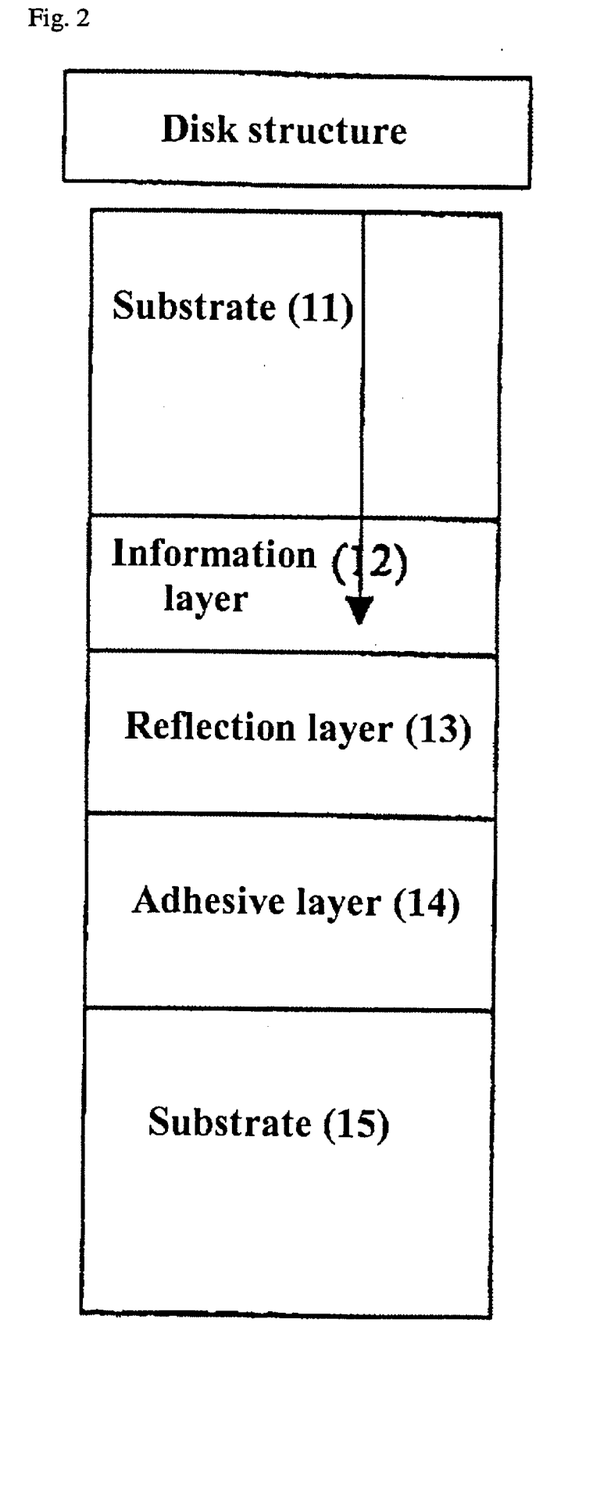

Alternatively, the optical data carrier has, for example, the following layer structure (cf. FIG. 2): a preferably transparent substrate (11), an information layer (12), if desired a reflection layer (13), if desired an adhesive layer (14), a further preferably transparent substrate (15).

Figure 3:
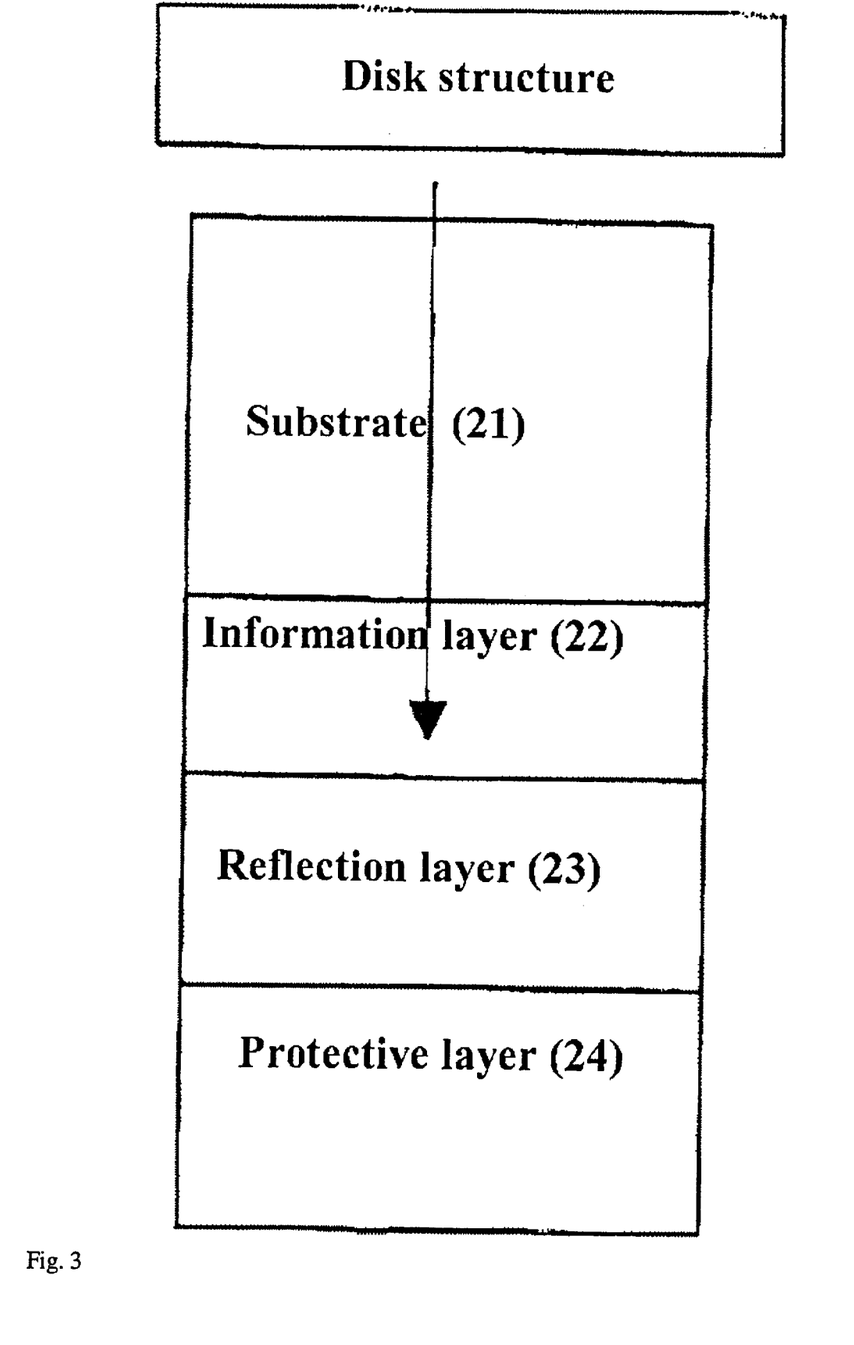

Alternatively, the optical data carrier has, for example, the following layer structure (cf. FIG. 3): a preferably transparent substrate (21), an information layer (22), if desired a reflection layer (23), a protective layer (24).

The invention further provides optical data carriers according to the invention which have been written on by means of blue, red or infrared light, in particular laser light, in particular infrared laser light.

The following examples illustrate the subject-matter of the invention.

EXAMPLES

The following preparative examples demonstrate the preparation of the dyes to be used according to the invention.

Example 1

11.5 g of cobalt phthalocyanine were introduced at room temperature into 700 ml of dry ethanol. 19.5 g of KCN were added and the mixture was refluxed for 6 hours. After cooling to RT, the mixture is filtered with suction and the solid is washed with water and ethanol. The dye obtained is dried under reduced pressure.

This gave 12.5 g of dye of the formula $\lambda_{max}$ 689 nm (NMP).

The following compounds were prepared analogously, using other cobalt phthalocyanines in the same molar amount.

| Example | $R^1$ and $R^2$ | $R^3$ α-substituent | $R^4$ | $R^5$ | $R^6$ | $\lambda_{max}$ nm (NMP) |
|---|---|---|---|---|---|---|
| 2 | CN | (tert-butyl)$_4$ | H | H | H | 704 |
| 3 | CN | (tert-butyl)$_4$ | Br$_4$ | H | H | 708 |
| 4 | CN | (tert-butyl)$_4$ | Br$_3$ | Cl | H | 707 |
| 5 | CN | (methoxyethoxy-ethoxy)$_4$ | H | H | H | 699 |
| 6 | CN | (2,4-dimethyl-3-pentoxy)$_4$ | H | H | H | 708 |
| 7 | CN | (2,4-dimethyl-3-pentoxy)$_4$ | Br$_2$ | H | H | 710 |
| 8 | CN | (tert-butyl)$_4$ | Br$_3$ | Cl | CH$_2$OFe | 715 |
| 9 | CN | (SO$_2$NCH$_2$ CH$_2$ O CH$_2$ CH$_2$ O CH$_3$)$_4$ | H | H | H | 669 |
| 10 | CN | (butoxy)$_4$ | H | H | (butoxy)$_4$ | 739 |
| 11 | CN | (2-butylthio)$_4$ | H | H | H | 711 |
| 12 | CN | (3-methylbutyl)$_4$ | H | H | (3-methylbutyl)$_4$ | 706 |
| 13 | CN | (2,4-dimethyl-3-pentoxy)$_3$ (butoxy) | H | H | butoxy | 708 |
| 14 | CN | (3-methylbut-2-ylthio)$_4$ | H | H | H | 714 |
| 15 | CN | 2,4-dimethyl-3-pentoxy)$_{2.5}$ (butoxy)$_{1.5}$ | H | H | (butoxy)$_{1.5}$ | 712 |
| 16 | CN | 2,4-dimethyl-3-pentoxy)$_2$ (butoxy)$_2$ | H | H | (butoxy)$_2$ | 722 |

Fe = Ferrocenyl

Example 17

11.5 g of cobalt phthalocyanine were introduced at room temperature into 700 ml of dry ethanol. 29.5 g of KSCN were added and the mixture was refluxed for 10 hours. After cooling to RT, the mixture is filtered with suction and the solid is washed with water and ethanol. The dye obtained is dried under reduced pressure.

This gave 10.5 g of dye of the formula $\lambda_{max}$ 687 nm (NMP).

Example 18

11.5 g of cobalt phthalocyanine were introduced at room temperature into 700 ml of dry ethanol. 31 g of potassium tert-butoxide were added and the mixture was refluxed for 10 hours. After cooling to RT, the mixture is filtered with suction and the solid is washed with water and ethanol. The dye obtained is dried under reduced pressure.

This gave 8.5 g of dye of the formula $\lambda_{max}$ 685 nm (NMP).

Example 19

5 g of dye from Example 6 were introduced at room temperature into 700 ml of dry ethanol. 0.5 g of lithium perchlorate was added and the mixture was stirred at RT for 12 hours. After cooling to 5° C., the mixture is filtered with suction. The solution is evaporated to dryness on a rotary evaporator. The residue is suspended in water, filtered off with suction and washed with water. The dye obtained is dried under reduced pressure.

This gave 4.1 g of dye of the formula $\lambda_{max}$ 709 nm (NMP).

Example 20

11 g of dye from Example 6 were introduced at room temperature into 1 l of dry ethanol. 3 g of ferrocenium tetrafluoroborate were added and the mixture was stirred at RT for 12 hours. The dye which has precipitated is filtered off with suction. The dye obtained is dried under reduced pressure.

This gave 4.1 g of dye of the formula $\lambda_{max}$ 711 nm (NMP).

Example 21

10 g of tetra-α-(2,4-dimethyl-3-pentoxy)-Co-phthalocyanine were introduced at room temperature into 500 ml of dry ethanol. 3.6 g of tetraethylammonium cyanide were added and the mixture was refluxed for 8 hours. After cooling, the mixture is poured into water and filtered with suction. The residue is washed with water. The dye obtained is dried under reduced pressure.

This gave 11 g of dye of the formula $\lambda_{max}$ 707 nm (NMP).

Example 22

10 g of tetra-α-(2,4-dimethyl-3-pentoxy)-Co-phthalocyanine were introduced at room temperature into 500 ml of dry ethanol. 4.5 g of tetrabutylammonium cyanide were added and the mixture was refluxed for 8 hours. After cooling, the mixture is poured into water and filtered with suction. The residue is washed with water. The dye obtained is dried under reduced pressure.

This gave 11 g of dye of the formula $\lambda_{max}$ 706 nm (NMP).

Example 23

10 g of tetra-α-(2-butylthio)-Co-phthalocyanine were introduced at room temperature into 500 ml of dry ethanol. 4.5 g of tetrabutylammonium cyanide were added and the mixture was refluxed for 8 hours. After cooling, the mixture is poured into water and filtered with suction. The residue is washed with water. The dye obtained is dried under reduced pressure.

This gave 12 g of dye of the formula $\lambda_{max}$ 711 nm (NMP).

Example 24

A 3.8% strength solution of the dye from Example 6 in 2,2,3,3-tetrafluoropropanol was prepared at room temperature. This solution was applied by means of spin coating to a pregrooved polycarbonate substrate. The pregrooved polycarbonate substrate had been produced as a disk by means of injection moulding. The dimensions of the disk and the groove structure corresponded to those customarily used for CD-Rs. The disk with the dye layer as information carrier was coated with 100 nm of Ag by vapour deposition. A UV-curable acrylic coating composition was subsequently applied by spin coating and cured by means of a UV lamp. After the disk had been written on in a commercial test writing apparatus for CD-Rs (Pulstec OMT 2000×4) at a writing power of 6 mW and a simple writing rate (1.4 m/s), reading the information gave a modulation height of 75% (>60% is the specification for CD-Rs) for the 11T signal.

Example 25

A 3.8% strength solution of the dye from Example 19 in 2,2,3,3-tetrafluoropropanol was prepared at room temperature. This solution was applied by means of spin coating to a pregrooved polycarbonate substrate. The pregrooved polycarbonate substrate had been produced as a disk by means of injection moulding. The dimensions of the disk and the groove structure corresponded to those customarily used for CD-Rs. The disk with the dye layer as information carrier was coated with 100 nm of Ag by vapour deposition. A UV-curable acrylic coating composition was subsequently applied by spin coating and cured by means of a UV lamp. After the disk had been written on in a commercial test writing apparatus for CD-Rs (Pulstec OMT 2000×4) at a writing power of 6 mW and a simple writing rate (1.4 m/s), reading the information gave a modulation height of 73% (>60% is the specification for CD-Rs) for the 11T signal.

What is claimed is:

1. Optical data carrier comprising a preferably transparent substrate which may, if desired, have previously been coated with one or more reflection layers and to whose surface a light-writeable information layer, if desired one or more reflection layers and if desired a protective layer or a further substrate or a covering layer have been applied, which can be written on and read by means of infrared light, preferably laser light, particularly preferably light having a wavelength in the range 750–800 nm, in particular 770–790 nm, where the information layer comprises a light-absorbent compound and, if desired, a binder, characterized in that at least one cobalt(III) phthalocyanine in which the Co metal centre bears two axial substituents $R^1$ and $R^2$ which represent, independently of one another, CN, SCN, alkoxy or alkylthio is used as light-absorbent compound.

2. Optical data carrier comprising, as light-absorbent compound, a phthalocyanine of the formula I where

CoPc represents cobalt(III) phthalocyanine, where $R^1$ and $R^2$ are axial radicals and the radicals $R^3$ to $R^6$ correspond to substituents of the phthalocyanine, where

$R^1$ and $R^2$ represent, independently of one another, CN, SCN, alkoxy or alkylthio, $R^3$, $R^4$, $R^5$ and $R^6$ represent, independently of one another, halogen, cyano, alkyl, aryl, alkylamino, dialkylamino, alkoxy, aryloxy, arylthio, alkylthio, $SO_3H$, $SO_2NR^7R^8$, $CO_2R^{12}$, $CONR^7R^8$, $NH-COR^{12}$ or a radical $-(B)_m-D$, B is a bridge member selected from the group consisting of a direct bond, $CH_2$, CO, CH(alkyl), C(alkyl)$_2$, NH, S, O or $-CH=CH-$, where $(B)_m$ is a chemically realistic sequence of bridge members B and m represents a number from 1 to 10, preferably 1, D represents the monovalent radical of a redox system of the formula or represents a metallocenyl radical or metallocenyl carbonyl radical in which the metal centre can be titanium, manganese, iron, ruthenium or osmium,

$X^1$ and $X^2$ represent, independently of one another, NR'R", OR" or SR", $Y^1$ represents NR', O or S, $Y^2$ represents NR', n represents a number from 1 to 10 and R' and R" represent, independently of one another, hydrogen, alkyl, cycloalkyl, aryl or hetaryl or form a direct bond or a bridge to one of the carbon atoms of the chain, w, x, y and z represent, independently of one another, numbers from 0 to 4 and $w+x+y+z \leq 12$, $R^7$ and $R^8$ represent, independently of one another, alkylamino, hydroxyalkylamino, dialkylamino, bishydroxyalkylamino or arylamino or $R^7$ and $R^8$ together with the N atom to which they are bound form a heterocyclic 5-, 6- or 7-membered ring, with or without participation of further heteroatoms, in particular from the group consisting of O, N and S, where $NR^7R^8$ represents, in particular, pyrrolidino, piperidino or morpholino, and Kat$^+$ represents a cation, and $R^{12}$ represents alkyl, aryl, hetaryl or hydrogen.

3. Optical data carrier according to claim 1 or 2, characterized in that the light-writeable information layer comprises at least one cobalt phthalocyanine of the formula I in which, for the radicals $R^1$ to $R^8$, R, R', R", $R^{12}$:

Alkyl substituents are $C_1$–$C_{16}$-alkyl, in particular $C_1$–$C_6$-alkyl, which may be unsubstituted or substituted by halogen such as chlorine, bromine or fluorine, hydroxy, cyano and/or $C_1$–$C_6$-alkoxy, Alkoxy substituents are $C_1$–$C_{16}$-alkoxy, in particular $C_1$–$C_6$-alkoxy which may be unsubstituted or substituted by halogen such as chlorine, bromine or fluorine, hydroxy, cyano and/or $C_1$–$C_6$-alkyl, Cycloalkyl substituents are preferably $C_4$–$C_8$-cycloalkyl, in particular $C_5$–$C_6$-cycloalkyl, which may be unsubstituted or substituted by halogen such as chlorine, bromine or fluorine, hydroxy, cyano and/or $C_1$–$C_6$-alkyl, Alkenyl substituents are preferably $C_6$–$C_8$-alkenyl, which may be unsubstituted or substituted by halogen such as chlorine, bromine or fluorine, hydroxy, cyano and/or $C_1$–$C_6$-alkyl, where alkenyl is particularly preferably allyl, Hetaryl substituents are preferably heterocyclic radicals having 5- to 7-membered rings which preferably contain heteroatoms from the group consisting of N, S and/or O and may be fused to aromatic rings or may bear further substituents, for example halogen, hydroxy, cyano and/or alkyl, with particular preference being given to: pyridyl, furyl, thienyl, oxazolyl, thiazolyl, imidazolyl, quinolyl, benzoxazolyl, benzothiazolyl and benzimidazolyl, Aryl substituents are $C_6$–$C_{10}$-aryl, preferably phenyl or naphthyl, which may be unsubstituted or substituted by halogen such as F or Cl, hydroxy, $C_1$–$C_6$-alkyl, $C_1$–$C_6$-alkoxy, $NO_2$ and/or CN.

4. Optical data carrier according to claim 1, characterized in that the cobalt phthalocyanine has the formula Ic.

5. Optical data carrier according to claim 1, characterized in that the light-writeable information layer comprises at least one cobalt phthalocyanine of the formula I in which $R^3$, $R^4$, $R^5$ and $R^6$ represent, independently of one another, chlorine, fluorine, bromine, iodine, cyano, methyl, ethyl, propyl, isopropyl, butyl, isobutyl, tert-butyl, pentyl, tert-amyl, hydroxyethyl, 3-dimethylaminopropyl, 3-diethylaminopropyl, phenyl, p-tert-butylphenyl, p-methoxyphenyl, isopropylphenyl, trifluoromethylphenyl, naphthyl, methylamino, ethylamino, propylamino, isopropylamino, butylamino, isobutylamino, tert-butylamino, pentylamino, tert-amylamino, benzylamino, methylphenylhexylamino, hydroxyethylamino, aminopropylamino, aminoethylamino, 3-dimethylaminopropylamino, 3-diethylaminopropylamino, diethylaminoethylamino, dibutylaminopropylamino, morpholinopropylamino, piperidinopropylamino, pyrrolidinopropylamino, pyrrolidonopropylamino, 3-(methylhydroxyethylamino)-propylamino, methoxyethylamino, ethoxyethylamino, methoxypropylamino, ethoxypropylamino, methoxyethoxypropylamino, 3-(2-ethylhexyloxy)propylamino, isopropyloxypropylamino, dimethylamino, diethylamino, diethanolamino, dipropylamino, diisopropylamino, dibutylamino, diisobutylamino, di-tert-butylamino, dipentylamino, di-tert-amylamino, bis(2-ethylhexyl)amino, bis(aminopropyl)amino, bis(aminoethyl)amino, bis(3-dimethylaminopropyl)amino, bis(3-diethylaminopropyl)amino, bis(diethylaminoethyl)amino, bis(dibutylaminopropyl)amino, di(morpholinopropyl)amino, di(piperidinopropyl)amino, di(pyrrolidinopropyl)amino, di(pyrrolidonopropyl)amino, bis(3-(methylhydroxyethylamino)propyl)amino, dimethoxyethylamino, diethoxyethylamino, dimethoxypropylamino, diethoxypropylamino, di(methoxyethoxyethyl)amino, di(methoxyethoxypropyl)amino, bis(3-(2-ethylhexyloxy)propyl)amino, di(isopropyloxyisopropyl)amino, methoxy, ethoxy, propyloxy, isopropyloxy, butyloxy, isobutyloxy, tert-butyloxy, pentyloxy, tert-amyloxy, methoxyethoxy, ethoxyethoxy, methoxypropyloxy, ethoxypropyloxy, methoxyethoxypropyloxy, 3-(2-ethylhexyloxy)propyloxy, phenyl, methylthio, ethylthio, propylthio, isopropylthio, butylthio, isobutylthio, tert-butylthio, pentylthio, tert-amylthio, methoxyphenyl, trifluoromethylphenyl, naphthyl, $CO_2R^{12}$, $CONR^7R^8$, $NH$—$COR^{12}$, $SO_3H$, $SO_2NR^7R^8$, or a radical of the formula where $(B)_m$ represents where the asterisk (*) indicates the point of linkage to the 5-membered ring, w, x, y and z represent, independently of one another, numbers from 0 to 4 and $w+x+y+z \leq 12$, $Kat^+$ represents a lithium cation, sodium cation, potassium cation, tetrabutylammonium cation, tetrapropylammonium cation, tetraethylammonium cation, tetramethylammonium cation, triethyloxonium cation, triphenylcarbonium cation, diphenyliodonium cation, N-ethylpyridinium cation or ferrocenium cation, $NR^7R^8$ represents amino, methylamino, ethylamino, propylamino, isopropylamino, butylamino, isobutylamino, tert-butylamino, pentylamino, tert-amylamino, benzylamino, methylphenylhexylamino, 2-ethyl-1-hexylamino, hydroxyethylamino, aminopropylamino, aminoethylamino, 3-dimethylaminopropylamino, 3-diethylaminopropylamino, morpholinopropylamino, piperidinopropylamino, pyrrolidinopropylamino, pyrrolidonopropylamino, 3-(methylhydroxyethylamino)propylamino, methoxyethylamino, ethoxyethylamino, methoxypropylamino, ethoxypropylamino, methoxyethoxypropylamino, 3-(2-ethylhexyloxy)propylamino, isopropyloxyisopropylamino, dimethylamino, diethylamino, dipropylamino, diisopropylamino, dibutylamino, diisobutylamino, di-tert-butylamino, dipentylamino, di-tert-amylamino, bis(2-ethylhexyl)amino, dihydroxyethylamino, bis(aminopropyl)amino, bis(aminoethyl)amino, bis(3-dimethylaminopropyl)amino, bis(3-diethylaminopropyl)amino, di(morpholinopropyl)amino, di(piperidinopropyl)amino, di(pyrrolidinopropyl)amino, di(pyrrolidonopropyl)amino, bis(3-(methylhydroxyethylamino)propyl)amino, dimethoxyethylamino, diethoxyethylamino, dimethoxypropylamino, diethoxypropylamino, di(methoxyethoxypropyl)amino, bis(3-(2-ethylhexyloxy)propyl)amino, di(isopropyloxyisopropyl)amino, anilino, p-toluidino, p-tert-butylanilino, p-anisidino, isopropylanilino or naphthylamino or $NR^7R^8$, in particular pyrrolidino, piperidino, piperazino or morpholino, $R^{12}$ represents hydrogen, methyl, ethyl, propyl, isopropyl, butyl, isobutyl, tert-butyl, pentyl, tert-amyl, phenyl, p-tert-butylphenyl, p-methoxyphenyl, isopropylphenyl, p-trifluoromethylphenyl, cyanophenyl, naphthyl, 4-pyridinyl, 2-pyridinyl, 2-quinolinyl, 2-pyrrolyl or 2-indolyl, where
the alkyl, alkoxy, aryl and heterocyclic radicals may, if desired, bear further radicals such as alkyl, halogen, hydroxy, hydroxyalkyl, amino, alkylamino, dialkylamino, nitro, cyano, CO—$NH_2$, alkoxy, alkoxycarbonyl, morpholino, piperidino, pyrrolidino, pyrrolidono, trialkylsilyl, trialkylsiloxy or phenyl, the alkyl and/or alkoxy radicals may be saturated, unsaturated, straight-chain or branched, the alkyl radicals may be partially halogenated or perhalogenated, the alkyl and/or alkoxy radicals may be ethoxylated or propoxylated or silylated, adjacent alkyl and/or alkoxy radicals on aryl or heterocyclic radicals may together form a three- or four-membered bridge.

6. Optical data carrier according to claim 1, characterized in that the light-writeable information layer additionally contains a metal-containing or metal-free phthalocyanine which is different from (I), where the central atom is selected from the group consisting of Si, Zn, Al, Cu, Pd, Pt, Au and Ag, in particular Cu or Pd.

7. Optical data carrier having an information layer which has been written on, obtainable by writing on the optical data carrier according to claim 1 by means of light having a wavelength of from 700 to 830 nm, preferably 750–b 800 nm.

8. Process for producing the optical data carrier according to claim 1, characterized in that the light-writeable information layer is applied to a transparent substrate by coating with the cobalt phthalocyanine of the formula I, if desired in combination with suitable binders, additives and suitable solvents, and this coated substrate is, if desired, provided with a reflection layer, if desired further intermediate layers and, if desired, a protective layer.

9. Use of cobalt phthalocyanines of the formula (I) as light-absorbent compounds in the light-writeable information layer of optical data stores.

10. Compounds of the formula Ic where
Halogen represents chlorine, bromine or fluorine,
Alkoxy represents $C_1$–$C_8$-alkoxy which may be substituted or unsubstituted and a is a number from 0 to 4, b is a number from 0 to 10, c is a number from 0 to 8, where the sum of a, b and c is $\leq 12$, and
$R^1$, $R^2$, $R^7$, $R^8$, $Kat^+$ and CoPc are as defined above.

11. Process for preparing the compound according to claim 10, characterized in that a cobalt phthalocyanine which is substituted by sulphonamide groups of the formula $SO_2NR^7R^8$, where $R^7$ and $R^8$ are as defined above, and may be substituted by halogen and/or alkoxy radicals is oxidized and reacted with KatCN, KatSCN, Katalkoxy or Katalkylthio.

12. Mixtures comprising
a) a cobalt(III) phthalocyanine whose Co metal centre bears two axial substituents $R^1$ and $R^2$ which represent, independently of one another, CN, SCN, alkoxy or alkylthio and
b) a phthalocyanine different from a), in particular a Co-free phthalocyanine.

* * * * *